United States Patent [19]

Furuno et al.

[11] 3,962,429

[45] June 8, 1976

[54] METHOD FOR REDUCING SIDE EFFECTS OF AMINOGLYCOSIDE ANTIBIOTICS AND COMPOSITION THEREFOR

[75] Inventors: Kouji Furuno, Kokubunji; Akira Okazaki, Oyama; Syuzo Matsubara, Fuchu; Motoharu Shiba, Omiya; Akitoshi Shioya, Kawagoe, all of Japan

[73] Assignee: Chugai Seiyaku Kabushiki Kaisha, Tokyo, Japan

[22] Filed: July 23, 1974

[21] Appl. No.: 491,171

[30] Foreign Application Priority Data

Aug. 1, 1973 Japan.............................. 48-85846

[52] U.S. Cl................................. 424/181; 424/180
[51] Int. Cl.² ...................... A01N 9/00; A01N 9/28
[58] Field of Search............ 424/279, 115, 180, 181

[56] References Cited
OTHER PUBLICATIONS

Chemical Abstracts, 68:103736c, (1968).

*Primary Examiner*—Albert T. Meyers
*Assistant Examiner*—D. W. Robinson
*Attorney, Agent, or Firm*—Browdy and Neimark

[57] ABSTRACT

Side effects of an aminoglycoside antibiotic, renal toxicity and 8th nerve toxicity, are reduced by administering a glucosaccharic acid as well as the aminoglycoside antibiotic. An improved method for treating bacterial infection using an aminoglycoside antibiotic and a pharmaceutical composition of an aminoglycoside antibiotic with reduced side effects are disclosed.

25 Claims, No Drawings

METHOD FOR REDUCING SIDE EFFECTS OF AMINOGLYCOSIDE ANTIBIOTICS AND COMPOSITION THEREFOR

This invention relates to a method for reducing the side effects of an aminoglycoside antibiotic and a novel pharmaceutical composition of an aminoglycoside antibiotic, the side effects of which are reduced.

An aminoglycoside antibiotic means generally an antibiotic having in its molecule either deoxystreptamine or streptamine structure to which amino sugar is bound by glycoside bond. The antibiotic has so strong activity in controlling gram-positive and -negative bacteria, acid fast bacteria, etc. that they are regarded as an important drug in view of practical uses.

The antibiotics exhibit a broad anti-bacterial spectrum in vitro, can control the proliferation of various pathogenic bacteria even at a very low concentration and also exhibit an excellent prophylactic activity against experimental infection of various pathogenic bacteria in mice. The antibiotics, however, exhibit 8th nerve and renal toxicities and their application has been limited. Especially, renal toxicity is regarded as a serious problem and it is statistically known, even in case of kanamycin which is thought as the antibiotic having the lowest toxicity among this series of antibiotics, that various indexes showing renal function become worse as the cumulative dose increases. Further, the antibiotic has never been administered to a patient having renal function disorder or to be given various plasma expanders, since serious or fatal disorder of renal function is often observed in such cases.

One object of this invention is to provide a method for reducing side effects of an aminoglycoside antibiotic, and another object is to provide a novel pharmaceutical composition containing an aminoglycoside antibiotic, the side effects of which are reduced. Other objects would appear from the description hereinbelow.

The first embodiment of this invention is a method for treating bacterial infection using an aminoglycoside antibiotic, characterized by administering as well as the aminoglycoside antibiotic a glucosaccharic acid to mammals including human beings or poultry in an amount of at least 50% by weight based on the free form of said antibiotic. The side effects of the aminoglycoside antibiotic, renal toxicity and 8th nerve toxicity, are reduced by such an embodiment.

The aminoglycoside antibiotic applied to this invention may be streptomycin, neomycin B and C, kanamycin A, B and C, ribostamycin, paromomycin I and II, a gentamicin complex, tobramycin, butirosin A and B, lividomycin A and B, 3′,4′-dideoxy-kanamycin B, sismomicin, 1-N-{(S)-4-amino-2-hydroxybutylyl}-3′,4′-dideoxy-kanamycin B, 1-N-{(S)-4-amino-2-hydroxybutylyl}-3′,4′-dideoxyneamine, 1-N-{(S)-4-amino-2-hydroxybutylyl}-kanamycin A and the like. The aminoglycoside antibiotic may be either free base or mineral acid addition salt, and there may be mentioned hydrochloric acid addition salt, sulfuric acid addition salt and the like as the examples of the mineral acid addition salt.

The glucosaccharic acid which may be used in this invention is free type glucosaccharic acid, glucosaccharo-1,4-lactone, glucosaccharo-6,3-lactone and glucosaccharo-1,4:6,3-dilactone, or their metal salts. The metal salt may be any of sodium salt, potassium salt, calcium salt and the like.

The glucosaccharic acid is to be used in an amount of at least 50% by weight based on the free form of the aminoglycoside antibiotic as a lower limit in view of side effects-reducing effect, while the upper limit is not critical because of the very low toxicity of the glucosaccharic acid. It is preferable to use 100–1,000% by weight of the glucosaccharic acid based on the free form of the antibiotic.

The aminoglycoside antibiotic is usually administered by an intramuscular injection in the form of an aqueous solution, and renal function disorder occurs frequently in such a case. It is therefore most preferable to administer the glucosaccharic acid by intramuscular injection in the form of the mixture of the aminoglycoside antibiotic and the glucosaccharic acid. However, these two materials may also be administered through different administration routes from each other; for example, the aminoglycoside antibiotic by intramuscular injection and the glucosaccharic acid through oral route, etc. The two materials may be administered separately at two different times if the interval is not too long, with the same effect as obtainable by the simultaneous administration.

The method for treating bacterial infection using an aminoglycoside antibiotic according to this invention may be applied to any animal such as human beings, monkeys, horses, bovines, dogs, cats, chickens, pigs, sheep and the like to which an aminoglycoside antibiotic may be applied.

The second embodiment of this invention is a pharmaceutical composition of an aminoglycoside antibiotic, the side effects of which are reduced, characterized by incorporating a glucosaccharic acid into the composition in an amount of at least 50% by weight based on the free form of the aminoglycoside antibiotic.

The aminoglycoside antibiotic and the glucosaccharic acid which may be used in this embodiment are the same as stated hereinbefore.

The aminoglycoside antibiotic is not absorbed through a digestive tract and is usually administered in the form of a parenteral injection, with the exception that the antibiotic is used to treat bacterial infection in a digestive tract. The composition of this embodiment is also administered usually in the form of a parenteral injection.

The parenteral injection may be prepared by a conventional method. That is, the aminoglycoside antibiotic and the glucosaccharic acid are mixed thoroughly in a mortar, and the mixture is filled in a vial and the vial is well stoppered; or they are dissolved in water and the aqueous solution is filled in an ampule and the ampule is melt-sealed.

The glucosaccharic acid is not so stable so that it is preferable to add methionine to the parenteral injection as a stabilizer, and more preferably to add one more stabilizer, a compound which releases $SO_3^{--}$ ion in an aqueous state, e.g. sulfites, thiosulfates, hydrosulfites, acid bisulfites, metabisulfites and Rongalite (formaldehyde sodium sulfoxylate), in addition to methionine.

In case the aminoglycoside antibiotic and the glucosaccharic acid are dissolved in water to make a parenteral injection in the form of aqueous solution, the solution may be filled in a vial instead of filling in an ampule and freeze-dried. This parenteral injection is excellent in preservability, but it is also preferable to add methionine and a compound which releases $SO_3^{--}$ ion in an aqueous state as a stabilizer. It is possible to give the preparation good appearance by further adding a sugar, e.g. mannite, or an amino acid, e.g. arginine.

The amount of the glucosaccharic acid to be incorporated into the pharmaceutical composition of the aminoglycoside antibiotic is at least 50%, preferably 100–1,000%, by weight based on the free form of said antibiotic. The pH of the composition is preferably adjusted to around neutral, i.e. 6.5–7.5.

In both embodiments of this invention stated above, the aminoglycoside antibiotic is believed to react partially with the glucosaccharic acid to form a salt, since the aminoglycoside antibiotic has a few amino groups in its molecule and the glucosaccharic acid has one or two carboxyl groups in its molecule or forms one or two carboxyl groups in an aqueous state. However, the side effect-reducing effect of the aminoglycoside antibiotic is not effected adversely whether it reacts with the glucosaccharide to form a salt or not.

The invention will be further explained by the following Examples, but they are not to be construed as limiting the scope of this invention.

EXAMPLE 1 a. Effects of a glucosaccharic acid against renal function disorder to be induced by kanamycin A sulfuric acid addition salt:

The Wister-Imamichi strain male rats (weighing 250–300 g) were used as test animals by dividing them into groups of 5 rats each.

After 48 hours of abstinence from water, each rat was intraperitoneally administered an 800 mg/kg dose of glucosaccharo-1,4-lactone sodium salt which had been dissolved in physiological saline solution, and 5 minutes after the administration, the rat was intramuscularly administered a 300 mg/kg dose of kanamycin A sulfuric acid addition salt as weight of free form. Twenty-four hours after the administration, renal function disorder and distribution of kanamycin in organs were observed. For control, the same amount of physiological saline solution was used instead of the glucosaccharic acid solution.

The results are shown in the following Tables 1 and 2.

Table 1

| | amount of urine (ml)[1] | occult blood in urine[2] | pH (urine) | renal edema (%)[3] | BUN[4] (mg/dl) |
|---|---|---|---|---|---|
| control | 4 | ~ | 7.0 | 0.92 | 80 |
| administered glucosaccharo-1,4-lactone.Na | 18 | +~± | 5.5 | 0.71 | 25 |

[1]Total amount of urine till 24 hours after the administration
[2]Measured with the use of testpapers "Labstix", testpaper for simultaneously detecting pH, protein, glucose, ketones, and occult blood. (manufactured by Miles and Sankyo)
[3](weight of kidneys/body weight) × 100 (%)
[4]urea-nitrogen content in blood; measured with the use of "U-NI-GRAPH", testpaper for detecting urea-nitrogen content in blood. (manufactured by Ono Yakuhin)

Table 2

| Time (hours) Organs measured | ½ | 1 | 3 | 9 | 24 | 48 |
|---|---|---|---|---|---|---|
| Blood | 810 | 630 | 140 | 47 | 1.4 | 0.35 |
| | 1100 | 400 | 65 | 0.1 | — | — |
| Kidney | 2730 | 2880 | 1330 | 1520 | 1750 | 1550 |
| | 1900 | 1150 | 850 | 560 | 450 | 330 |
| Liver | 14.5 | 9.2 | 4.9 | 4.1 | 3.5 | 3.3 |
| | 20.5 | 7.5 | 1.0 | — | — | — |
| Lung | 56.3 | 42.0 | 7.8 | 4.0 | 1.2 | 1.5 |
| | 43.3 | 24.7 | 2.8 | — | — | — |

(Note) The figures in the table indicate the weight of kanamycin A (mcg/g) as free form
Upper: Control group
Lower: Administered group of glucosaccharo-1,4-lactone.Na It is clearly shown in Tables 1 and 2 that the administration of the glucosaccharic acid significantly suppresses renal function disorder and promotes the excretion from blood and that the concentration of kanamycin in body is lower than that of the control and kanamycin is not locally accumulated in a specific organ.

b. Relationship between renal function disorder to be induced by kanamycin A sulfuric acid addition salt and the time of administration:

The Wister-Imamichi strain male rats (weighing 250–300 g) used were divided into groups of 5 rats each.

After 48 hours of abstinence from water, each rat was intramuscularly administered a 200 mg/kg dose of kanamycin A sulfuric acid addition salt as the weight of free form, and then intraperitoneally administered a 10% (w/v) aqueous solution of dextran (an average molecular weight: 40,000) in a dose of 30 ml/kg.

Glucosaccharo-1,4-lactone sodium salt was administered in a dose of 600 mg/kg at the same time, 10, 20, 30 and 40 minutes after the administration of the kanamycin. The renal function in each of the groups was observed 24 hours after the administration of the Kanamycin.

The results are shown in the following Table 3.

Table 3

| time after the administration of (kanamycin (minutes) | renal edema* (%) | BUN (mg/dl)* |
|---|---|---|
| simultaneous | 0.76 | 24 |
| 10 | 0.88 | 48 |
| 20 | 0.98 | 60 |
| 30 | 1.02 | 450 |
| 40 | 1.10 | 500 |

*determined in the same manner as in (a)

The results shown in Table 3 clearly exhibit that renal function disorder is completely suppressed by the administration of the glucosaccharic acid simultaneously with the Kanamycin A sulfuric acid addition salt-dextran and that as delying the time of administration of the glucosaccharic acid, suppression effects were lowered and, 30 minutes after the administration of the Kanamycin the effects could not essentially be observed.

c. Relationship between renal function disorder to be induced by Kanamycin A sulfuric acid addition salt and a dose level of a glucosaccharic acid:

The Wister-Imamichi strain male rats (weighing 250–300 g) used were divided into groups of 5 rats each.

After 48 hours of abstinence from water, each rat was intramuscularly administered Kanamycin A sulfuric acid addition salt in a dose of 200 mg/kg and then intraperitoneally administered a 10% (w/v) aqueous solution of dextran (an average molecular weight: 40,000) in a dose of 30 ml/kg. At the same time, the rat was intraperitoneally administered glucosaccharo-1,4-lactone sodium salt in a different dose, such as 25, 50, 100, 200, 400, and 800 mg/kg, and 24 hours after the administration renal function was measured.

The results are shown in the following Table 4.

Table 4

| dose (mg/kg) | renal edema* (%) | BUN* (mg/dl) |
| --- | --- | --- |
| 0 | 1.14 | 500 |
| 25 | 1.16 | 240 |
| 50 | 1.08 | 125 |
| 100 | 0.92 | 70 |
| 200 | 0.84 | 50 |
| 400 | 0.80 | 35 |
| 800 | 0.75 | 20 |

*determined in the same manner as in (a)

Table 4 shows that the side effects of the antibiotic are suppressed in a dose of more than 100 mg/kg and well suppressed in a dose of 200 mg/kg.

d. Influence of a glucosaccharic acid on the antibacterial activities of kanamycin sulfuric acid addition salt:

The ddY strain male mice (5 weeks old, weighing: 15–25±2 g) used as test animals were divided into groups of 10 mice each.

Each mouse was infected by the intraperitoneal administration with *Escherichia coli* ($4 \times 10^1$ cells and $4 \times 10^2$ cells) or *Klebsiella pneumoniae* ($2 \times 10^3$ cells). Twenty-five minutes after the administration, each mouse was intraperitoneally administered glucosaccharo-1,4-lactone sodium salt as a physiological saline solution in a dose of 20 mg/head and each of the control mice was administered the same amount of physiological saline solution. Five minutes after the administration, each mouse was subcutaneously administered kanamycin A sulfuric acid addition salt.

$ED_{50}$ of the tested mice was calculated by a Behrens-Kärber method.

The results are shown in Table 5.

Table 5

| | control | administered glucosaccharo-1,4-lactone.Na |
| --- | --- | --- |
| E. coli $4\times10^1$ | 10.0 (mg/kg) | 8.2 (mg/kg) |
| E. coli $4\times10^2$ | 13.8 | 12.0 |
| Kl.pneumoniae $2\times10^3$ | 21.6 | 24.0 |

From the results shown in Table 5, there is no significant difference in $ED_{50}$ of each of the groups, and the administration of the glucosaccharic acid does not affect on the antibacterial activity of the antibiotic.

e. Influence of the glucosaccharic acid upon acute toxicity of kanamycin A sulfuric acid addition salt:

The ddY strain mice (5 weeks old; weighing: 25±2 g) used as test animals were divided into groups of 4 mice each.

Each mouse of the test group was administered a 20 mg/head dose of glucosaccharo-1,4-lactone sodium salt in physiological saline solution and each mouse of the control group was administered the same volume of physiological saline solution. Five minutes after the administration, the mice were administered kanamycin A sulfuric acid addition salt and $LD_{50}$ of the mice was determined.

The results are shown in the following Table 6.

Table 6

| | control | administered glucosaccharo-1,4-lactone.Na |
| --- | --- | --- |
| subcutaneous | 2000 mg/kg | 2200 mg/kg |
| intraperitoneal | 1850 mg/kg | 1300 mg/kg |

From the results shown in Table 6, the administration of the glucosaccharic acid does not affect on acute toxicity of kanamycin A sulfuric acid addition salt.

EXAMPLE 2

The Wister-Imamichi strain male rats (weighing: 250–300 g) used as the test animal were divided into groups of five rats each.

After 48 hours of abstinence from water, each rat of the groups was intraperitoneally administered glucosaccharo-6,3-lactone sodium salt or glucosaccharo-1,4:6,3 dilactone as a solution of physiological saline solution in a dose of 800 mg/kg and 5 minutes after the administration the rats were intramuscularly administered kanamycin A sulfuric acid addition salt in a dose of 300 mg/kg as weight of free form. Twenty-four hours after the administration of the kanamycin, renal function was observed.

Each rat of the control group was treated administered the same volume of a physiological saline solution instead of the solution of the Kanamycin.

The results are shown in the following Table 7.

Table 7

| | renal edema* (%) | BUN* (mg/dl) |
| --- | --- | --- |
| control | 0.98 | 90 |
| administered glucosaccharic acid-6,3-lactone.Na | 0.74 | 33 |
| administered glucosaccharic acid-1,4:6,3-dilactone.Na | 0.76 | 35 |

*determined in the same manner as in (a)

EXAMPLE 3

To the Wister-Imamichi strain rats (weighing: 250–300 g), after 48 hours of abstinence from water, were intraperitoneally administered a 600 mg/kg dose of glucosaccharo-1,4-lactone sodium salt as a physiological saline solution, and five minutes after the administration a different kind of the aminoglycoside antibiotic was intramuscularly administered.

Twenty-four hours after the administration, renal function disorder of the rats was observed. For control, physiological saline solution was used instead of the solution of the glucosaccharic acid.

The results are shown in Table 8.

Table 8

| Antibiotics | Dose (mg as free form) | renal* edema (%) | BUN* (mg/dl) |
| --- | --- | --- | --- |
| kanamycin B | 200 | 0.76 | 35 |
| | | 0.98 | 120 |
| neomycin | 75 | 0.78 | 35 |
| | | 1.15 | 150 |
| streptomycin | 150 | 0.69 | 27 |
| | | 0.81 | 60 |

Table 8-continued

| Antibiotics | Dose (mg as free form) | renal* edema (%) | BUN* (mg/dl) |
|---|---|---|---|
| ribostamycin | 400 | 0.75 | 30 |
|  |  | 0.99 | 95 |
| paromomycin | 200 | 0.72 | 25 |
|  |  | 1.06 | 150 |
| gentamicin | 50 | 0.71 | 23 |
|  |  | 0.82 | 60 |

*determined in the same manner as in (a)
upper: administered group
lower: control group Table 8 shows that renal function disorder is well suppressed by the administration of glucosacchao-1,4-lactone sodium salt in addition to the antibiotic in every case.

EXAMPLE 4

1000 mg of germ free kanamycin A sulfuric acid addition salt as weight of free form, 500 mg of D-glucosaccharo-1,4-lactone sodium salt, 50 mg of methionine and 50 mg of Rongalite were mixed in a mortar, and the mixture was filled in a vial and melt-sealed. The preparation was used in the same manner as in the use of kanamycin A sulfuric acid addition salt.

EXAMPLE 5

500 mg of D-glucosaccharo-1,4-lactone sodium salt and 50 mg of methionine were dissolved in 5 ml of distilled water at 5°C, and to the resulting solution were added and dissolved 1000 mg of kanamycin A sulfuric acid addition salt and 50 mg of Rongalite. After adjusting the pH of the solution to 6.5, it was put in an ampule and the ampule was melt-sealed. The preparation was used in the same manner as in the use of kanamycin A sulfuric acid addition salt.

EXAMPLE 6

In 5 ml of distilled water at 5°C were dissolved 1,200 mg of D-glucosaccharo-1,4-lactone sodium salt and 80 mg of methionine followed by 1000 mg of kanamycin A sulfuric acid addition salt as weight of free form. The mixture was filled in a vial and immediately freeze-dried. The preparation was dissolved in 5 ml of parenteral distilled water just before the use and was intramuscularly administered in the same manner as in the use of kanamycin A sulfuric acid addition salt.

EXAMPLE 7

| | |
|---|---|
| kanamycin A sulfuric acid addition salt | 500 mg (as weight of free form) |
| D-glucosaccharo-1,4-lactone sodium salt | 500 mg |
| methionine | 50 mg |
| Rongalite | 100 mg |
| distilled water | 4 ml (q.s.) |

The composition above was mixed, the pH adjusted to 6.5, and filled in a vial. The vial was stoppered and the contents were freeze-dried. The preparation was dissolved in 4 ml of parenteral distilled water just before the use and administered in the same manner as in the use of kanamycin A sulfuric acid addition salt.

EXAMPLE 8

Example 6 was repeated except that 200 mg of kanamycin B sulfuric acid addition salt as weight of free form was used instead of 1,000 mg of kanamycin B sulfuric acid addition salt. The resulting preparation was dissolved in parenteral distilled water just before administration and used in the same manner as in the use of kanamycin B.

EXAMPLE 9

Example 7 was repeated except that 50 mg of gentamicin instead of 500 mg of kanamycin A sulfuric acid addition salt and D-glucosaccharo-6,3-lactone sodium salt instead of glucosaccharo-1,4-lactone sodium salt were used to form a preparation. The preparation was administered in the same manner as in the use of gentamicin.

EXAMPLE 10

Example 7 was repeated except that 350 mg of paromomycin sulfuric acid addition salt as weight of free form instead of 500 mg of kanamycin A sulfuric acid addition salt and D-glucosaccharo-1,4:6,3-dilactone for glucosaccharo-1,4-lactone sodium salt were used to form a preparation. The preparation was administered in the same manner as in the use of paromomycin.

EXAMPLE 11

Example 7 was repeated except that 500 mg of streptomycin sulfuric acid addition salt as weight in the free form instead of 500 mg of kanamycin A sulfuric acid addition salt and D-glucosaccharo-6,3-lactone sodium salt instead of glucosaccharo-1,4-lactone sodium salt. The resulting preparation was administered in the same manner as in the use of streptomycin.

EXAMPLE 12

| | |
|---|---|
| neomycin sulfuric acid addition salt | 20 mg (as weight in the free form) |
| D-glucosaccharo-1,4-lactone sodium salt | 100 mg |
| methionine | 10 mg |
| Rongalite | 20 mg |
| distilled water | 4 ml (q.s.) |

The composition above was mixed followed by adjusting the pH of the mixture to 6.5. Immediately after the mixture was filled in a vial and the vial was stoppered, the content was freeze-dried. The preparation was dissolved in 4 ml of parenteral distilled water just before the use and administered in the same manner as in the use of neomycin.

What is claimed is:

1. A method for treating bacterial infection and reducing the side effects of such treatment, comprising administering to mammals, in an amount sufficient to treat bacterial infection, both glucosaccharo-1,4-lactone, glucosaccharo-6,3-lactone, or the sodium, potassium or calcium salt of one of said lactones, and an aminoglycoside antibiotic selected from the group consisting of streptomycin, neomycin B and C, kanamycin A, B and C, ribostamycin, paromomycin I and II, a gentamicin complex, tobramycin, butirosin A and B, lividomycin A and B, 3', 4'-dideoxy-kanamycin B, sismomicin, 1-N-{(S)-4-amino-2-hydroxybutylyl}-3',4'-dideoxy-kanamycin B, 1-N-{(S)-4-amino-2-hydroxybutylyl}-3',4'-dideoxyneamine, 1-N-{(S)-4-amino-2-hydroxybutylyl} kanamycin A and mineral acid addition salts thereof, wherein said lactone or salt is used in an amount of from 50–1000% by weight of the antibiotic used based on the free form of the amino-glycoside antibiotic.

2. The method for treating bacterial infection in accordance with claim 1, wherein said mineral acid addition salts are sulfuric acid addition salts or hydrochloric acid addition salts.

3. A method in accordance with claim 1, wherein said aminoglycoside antibiotic is gentamicin complex.

4. A method in accordance with claim 1 wherein said aminoglycoside antibiotic and said lactone or salt are administered in the form of a mixture by intramuscular injection.

5. A method in accordance with claim 4, wherein said aminoglycoside antibiotic is gentamicin complex.

6. A method in accordance with claim 1 wherein said aminoglycoside antibiotic is administered through a different administration route than said lactone or salt.

7. The method for treating bacterial infection in accordance with claim 6, wherein the mineral acid addition salts are sulfuric acid addition salts or hydrochchloric acid addition salts.

8. A method in accordance with claim 6, wherein said aminoglycoside antibiotic is gentamicin complex.

9. The method for treating bacterial infection in accordance with claim 6, wherein said aminoglycoside antibiotic is administered by intramuscular injection in the form of an aqueous solution and said lactone or salt is orally administered.

10. A method in accordance with claim 9 wherein said aminoglycoside antibiotic is gentamicin complex.

11. A pharmaceutical composition for treating bacterial infection and reducing the side effects of such treatment, comprising an aminoglycoside antibiotic selected from the group consisting of streptomycin, neomycin B and C, kanamycin A, B and C, ribostamycin, paromomycin I and II, gentamicin complex, tobramycin, butirosin A and B, lividomycin A and B, 3'4'-dideoxy-kanamycin B, sismomicin, 1-N-{(S)-4-amino-2-hydroxybutylyl}-3',4'-dideoxy-kanamycin B, 1-N-{(S)-4-amino-2-hydroxybutylyl}-3',4',-dideoxyneamine, 1-N-{(S)-4-amino-2-hydroxybutylyl} kanamycin A and mineral acid addition salts thereof, having compounded thereinto glucosaccharo-1,4-lactone, glucosaccharo-6,3-lactone or a sodium, potassium or calcium salt of one of said lactones, in an amount of from 50–1000% by weight of the antibiotic present based on the free form of the antibiotic.

12. The pharmaceutical composition in accordance with claim 11, wherein said mineral acid addition salts are sulfuric acid addition salts or hydrochloric acid addition salts.

13. The pharmaceutical composition in accordance with claim 11, wherein said aminoglycoside antibiotic is gentamicin complex.

14. The pharmaceutical composition in accordance with claim 11, wherein said aminoglycoside antibiotic is partially reacted with said lactone to form a salt.

15. The composition in accordance with claim 14, wherein said aminoglycoside antibiotic is gentamicin complex.

16. The pharmaceutical composition in accordance with claim 11, wherein said composition is freeze-dried.

17. The composition in accordance with claim 16, wherein said aminoglycoside antibiotic is gentamicin complex.

18. The pharmaceutical composition in accordance with claim 11, wherein said composition is in the form of a parenteral aqueous solution.

19. The composition in accordance with claim 18, wherein said aminoglycoside antibiotic is gentamicin complex.

20. The pharmaceutical composition in accordance with claim 11, wherein said composition is in the form of parenteral powder.

21. The composition in accordance with claim 20, wherein said aminoglycoside antibiotic is gentamicin complex.

22. The pharmaceutical composition in accordance with claim 11, further including a stabilizing amount of methionine as a stabilizer for the lactone or salt.

23. The composition in accordance with claim 22, wherein said aminoglycoside antibiotic is gentamicin complex.

24. The pharmaceutical composition in accordance with claim 22 further including a compound which releases $SO_3^{--}$ ions in an aqueous state selected from the group consisting of sulfites, thiosulfates, hydrosulfites, acid bisulfites, metabisulfites and formaldehyde sodium sulfoxylate.

25. The composition in accordance with claim 24 wherein said aminoglycoside antibiotic is gentamicin complex.

\* \* \* \* \*